United States Patent
Haga et al.

(10) Patent No.: US 7,999,103 B2
(45) Date of Patent: Aug. 16, 2011

(54) METAL COMPLEX COMPOUND AND ORGANIC ELECTROLUMINESCENCE DEVICE USING THE COMPOUND

(75) Inventors: Masa-aki Haga, Bunkyo-Ku (JP); Li-fen Yang, Bunkyo-Ku (JP); Masumi Itabashi, Bunkyo-Ku (JP); Misa Ashizawa, Bunkyo-Ku (JP); Fumio Okuda, Sodegaura (JP)

(73) Assignees: Chuo University, Hachioji-shi (JP); Idemitsu Kosan Co., Ltd., Tokyo (JP)

( * ) Notice: Subject to any disclaimer, the term of this patent is extended or adjusted under 35 U.S.C. 154(b) by 1245 days.

(21) Appl. No.: 11/608,494

(22) Filed: Dec. 8, 2006

(65) Prior Publication Data

US 2007/0138437 A1    Jun. 21, 2007

Related U.S. Application Data

(60) Provisional application No. 60/750,378, filed on Dec. 15, 2005.

(51) Int. Cl.
*C07F 15/00* (2006.01)
*H01L 51/50* (2006.01)

(52) U.S. Cl. ............... 546/2; 428/690; 313/504; 546/5; 546/6

(58) Field of Classification Search .................. 546/6, 5, 546/2; 428/690; 313/504
See application file for complete search history.

(56) References Cited

FOREIGN PATENT DOCUMENTS

JP    2005-310733    11/2005

OTHER PUBLICATIONS

U.S. Appl. No. 11/610,145, filed Dec. 13, 2006, Okuda.
Andrew J. Wilkinson, et al., "Luminescent Complexes of Iridium (III) Containing N, C, N-Coordinating Terdentate Ligands", Inorganic Chemistry, vol. 45, No. 21, 2006, pp. 8685-8699.

*Primary Examiner* — Charanjit Aulakh
(74) *Attorney, Agent, or Firm* — Oblon, Spivak, McClelland, Maier & Neustadt, L.L.P.

(57) ABSTRACT

Provided are an organic electroluminescence device whose wavelength of light emission is short and which can emit blue light having a high color purity, and a metal complex compound for realizing the device. The metal complex compound is of a specific structure having a partial structure including two tridentate ligands. The organic electroluminescence device includes: a pair of electrodes; and an organic thin film layer which has one layer or a plurality of layers including at least a light emitting layer and is disposed between the pair of electrodes. In the organic electroluminescence device, at least one layer of the organic thin film layer contains the metal complex compound. The organic electroluminescence device emits light by applying a voltage between both the electrodes.

22 Claims, 1 Drawing Sheet

METAL COMPLEX COMPOUND AND ORGANIC ELECTROLUMINESCENCE DEVICE USING THE COMPOUND

TECHNICAL FIELD

The present invention relates to a novel metal complex compound and an organic electroluminescence device using the compound, in particular, an organic electroluminescence device whose wavelength of light emission is shortened so that blue light emission is obtained, which exhibits high efficiency of light emission, and which has a long lifetime, and a metal complex compound for realizing the device.

BACKGROUND ART

Investigation has been vigorously conducted on the use of an organic electroluminescence (EL) device as a display device for color display that replaces liquid crystal in recent years. However, the performance of the organic EL device as a light emitting device is still insufficient to realize the enlargement of the screen size of a display device using the organic EL device. A green light emitting device using an ortho-metallized iridium complex (fac-tris(2-phenylpyridine)iridium), which is a phosphorescent material, as a light emitting material has been proposed as means for improving the performance of the organic EL device (Non-patent Document 1; Non-patent Document 2).

At present, the color of light emitted from an organic EL device utilizing phosphorescence (in other words, a phosphorescent EL device) has been limited to a green color, so the scope of application of the device as a color display is narrow, and the development of a device with improved light emitting property for any other color has been demanded. In particular, no blue light emitting device having an outer quantum yield in excess of 5% has been reported. If the blue light emitting device can be improved, a color display composed only of phosphorescent organic EL devices will be able to display full colors and a white color. Accordingly, the improvement makes great strides forward in putting a phosphorescent EL device to practical use.

At present, the development of a compound containing Ir as a phosphorescent complex has been vigorously conducted, and the following compound A has been known as a compound for a green light emitting device. On the other hand, the following compound B has been known as a compound for a blue light emitting device, but is not practical in terms of the lifetime and efficiency of a device formed of the compound. In view of the foregoing, there arises a need for developing another complex for a blue light emitting device. However, no factor other than the compound B capable of turning the color of light into a blue color has been found at present.

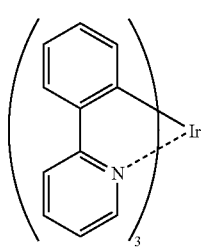

Compound A

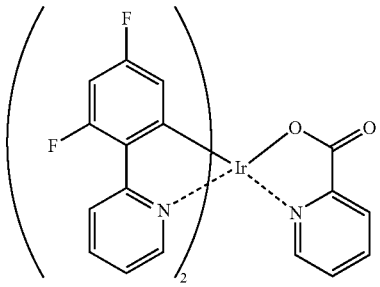

Compound B

The above-mentioned compounds belong to the group of complexes each using a bidentate chelate ligand. However, few complex using a tridentate chelate ligand similar to the bidentate ligand has been known, and only a compound C (Non-patent Document 3) and a compound D (Non-patent Document 4) shown below, and a few other examples have been known. However, the wavelength of light emission of each of those compounds is in a region of 585 to 600 nm, that is, a red color region, not in a blue color region. If a complex capable of emitting light in a blue color region can be realized by using the new tridentate ligand group, the realization will lead to the possibility of new technical development.

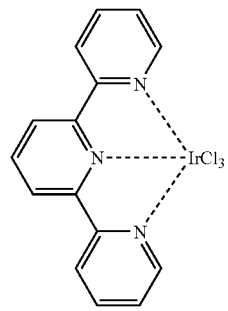

Compound C

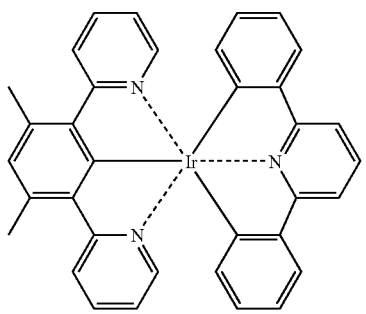

Compound D

[Non-patent Document 1] D. F. O'Brien and M. A. Baldo et al. "Improved energy transfer in electrophosphorescent devices" Applied Physics letters Vol. 74 No. 3, pp 442-444, Jan. 18, 1999

[Non-patent Document 2] M. A. Baldo et al. "Very high-efficiency green organic light-emitting devices based on electrophosphorescence" Applied Physics letters Vol. 75 No. 1, pp 4-6, Jul. 5, 1999

[Non-patent Document 3] J-P. Collin et al. J. Am. Chem. Soc., 121, 5009 (1999)

[Non-patent Document 4] J. A. G. Williams, Inorg. Chem., 43, 6513 (2004)

DISCLOSURE OF THE INVENTION

Problems to be Solved by the Invention

The present invention has been made with a view to solving the above-mentioned problems, and an object of the present invention is to provide an organic EL device whose wavelength of light emission is shortened so that blue light emission is obtained, which exhibits high efficiency of light emission, and which has a long lifetime, and a metal complex compound for realizing the device.

Means for Solving the Problems

The inventors of the present invention have revealed a new structural factor for turning the color of light into a blue color, in which the use of a metal complex compound included in any one of the following general formulae (1) to (4) having a partial structure having two tridentate chelate ligands shortens a wavelength of light emission so that blue light emission is obtained. Thus, the inventors of the present invention have completed the present invention.

In other words, the present invention provides a metal complex compound including a partial structure represented by one of the following general formulae (1) to (4) including tridentate chelate ligands.

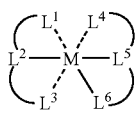
(1)

(In the general formula, a solid line represents a covalent bond, and a dotted line represents a coordinate bond.

M represents a trivalent metal atom belonging to Group 9 in the periodic table.

$L^1$ to $L^6$ each independently represent an aromatic hydrocarbon group which has 5 to 30 carbon atoms and which may have a substituent, a heterocyclic group which has 2 to 30 carbon atoms and which may have a substituent, or a group containing an atom belonging to any one of Groups 14 to 16 in the periodic table, and each of $L^2$ and $L^5$ is trivalent, $L^6$ is divalent, and each of $L^1$, $L^3$ and $L^4$ is monovalent. However, an element in each of $L^1$, $L^3$ and $L^4$ directly bonded to M is an atom belonging to Group 15 in the periodic table.)

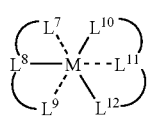
(2)

(In general formula, a solid line represents a covalent bond, and a dotted line represents a coordinate bond.

M represents a trivalent metal atom belonging to Group 9 in the periodic table.

$L^7$ to $L^{12}$ each independently represent an aromatic hydrocarbon group which has 5 to 30 carbon atoms and which may have a substituent, a heterocyclic group which has 2 to 30 carbon atoms and which may have a substituent, or a group containing an atom belonging to any one of Groups 14 to 16 in the periodic table, and each of $L^8$ and $L^{10}$ to $L^{12}$ is divalent, each of $L^7$ and $L^9$ is monovalent However, an element in each of $L^7$, $L^9$, and $L^{11}$ directly bonded to M is an atom belonging to Group 15 in the periodic table.

Further, the following structure is excluded from examples of the general formula (2);

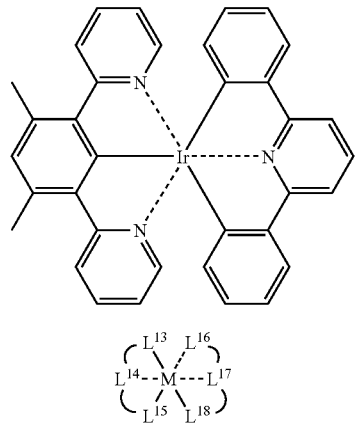
(3)

(In the general formula, a solid line represents a covalent bond, and a dotted line represents a coordinate bond.

M represents a trivalent metal atom belonging to Group 9 in the periodic table.

$L^{13}$ to $L^{18}$ each independently represent an aromatic hydrocarbon group which has 5 to 30 carbon atoms and which may have a substituent, a heterocyclic group which has 2 to 30 carbon atoms and which may have a substituent, or a group containing an atom belonging to any one of Groups 14 to 16 in the periodic table, and each of $L^{13}$ to $L^{15}$, and $L^{17}$ and $L^{18}$ is divalent, and $L^{16}$ is monovalent. However, an element in each of $L^{14}$, $L^{16}$, and $L^{17}$ directly bonded to M is an atom belonging to Group 15 in the periodic table.)

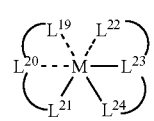
(4)

(In the general formula, a solid line represents a covalent bond, and a dotted line represents a coordinate bond.

M represents a trivalent metal atom belonging to Group 9 in the periodic table.

$L^{19}$ to $L^{24}$ each independently represent an aromatic hydrocarbon group which has 5 to 30 carbon atoms and which may have a substituent, a heterocyclic group which has 2 to 30 carbon atoms and which may have a substituent, or a group containing an atom belonging to any one of Groups 14 to 16 in the periodic table, and $L^{23}$ is trivalent, each of $L^{20}$, $L^{21}$, and $L^{24}$ is divalent, and each of $L^{19}$ and $L^{22}$ is monovalent. However, an element in each of $L^{19}$, $L^{20}$, and $L^{22}$ directly bonded to M is an atom belonging to Group 15 in the periodic table.)

According to the present invention, there is provided an organic EL device including an organic thin film layer which has one layer or a plurality of layers including at least a light emitting layer and is disposed between a pair of electrodes, in which: at least one layer of the organic thin film layer contains the metal complex compound; and light is emitted by applying a voltage between both the electrodes.

Effect of the Invention

The use of the metal complex compound of the present invention as a material for an organic EL device can provide an organic EL device whose wavelength of light emission is shortened so that blue light emission is obtained, which exhibits high efficiency of light emission, and which has a long lifetime.

BEST MODE FOR CARRYING OUT THE INVENTION

Figure 1:
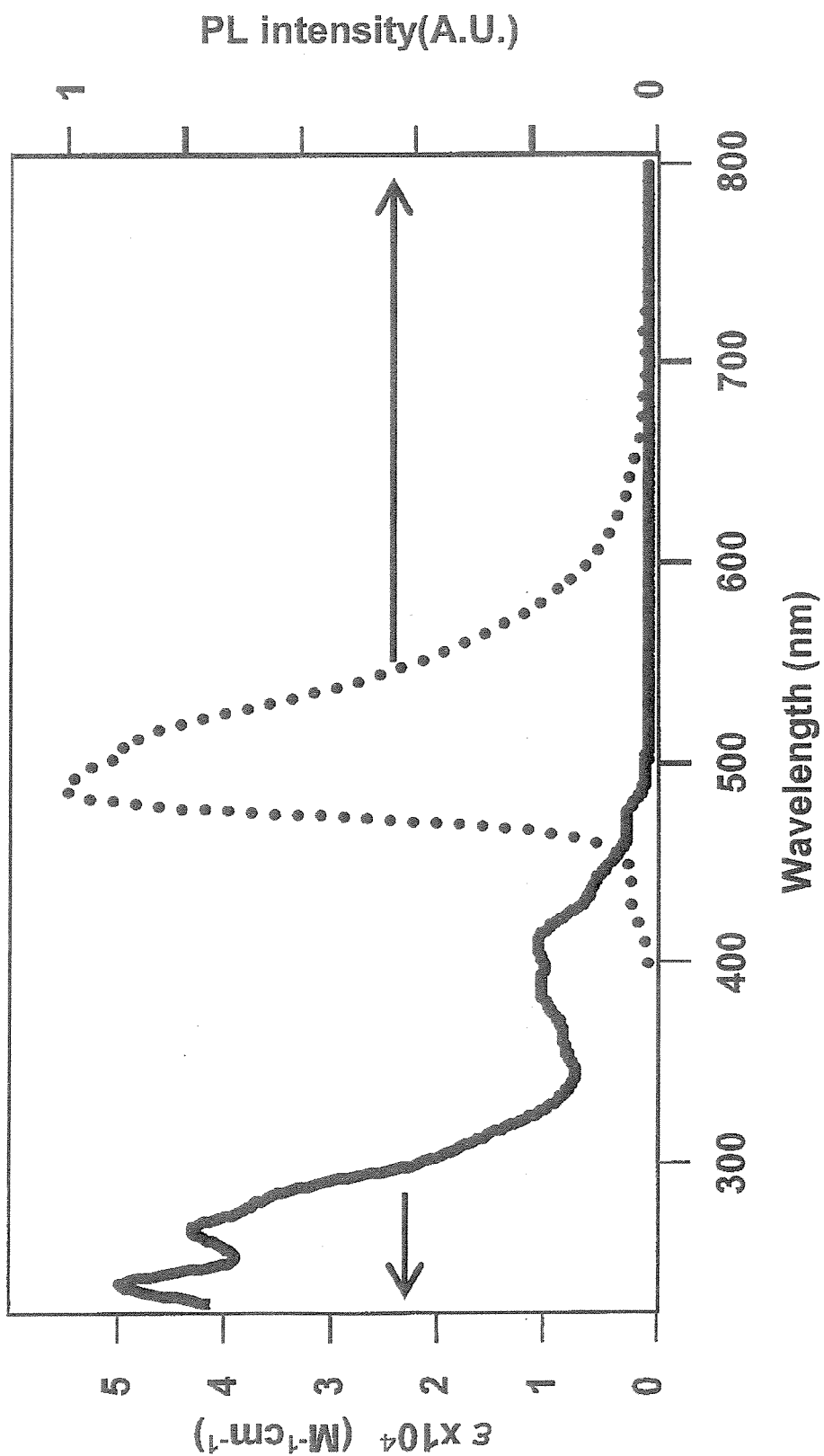
[FIG. 1] A view showing the UV-vis absorption/emission spectrum of a metal complex compound D of the present invention.

A metal complex compound of the present invention is a metal complex compound represented by the following general formula (1), (2), (3), or (4) having a tridentate chelate ligand.

In each of the general formulae (1) to (4), a solid line represents a covalent bond, and a dotted line represents a coordinate bond.

Hereinafter, a metal complex compound represented by the general formula (1) having two tridentate chelate ligands will be described first.

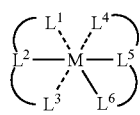
(1)

In the general formula (1), M represents a trivalent metal atom belonging to Group 9 in the periodic table. Examples of the trivalent metal atom include cobalt (Co), rhodium (Rh), and iridium (Ir) atoms. Of those, Ir is preferable.

In the general formula (1), $L^1$ to $L^6$ each independently represent an aromatic hydrocarbon group which has 5 to 30 carbon atoms and which may have a substituent, a heterocyclic group which has 2 to 30 carbon atoms and which may have a substituent, or a group containing an atom belonging to any one of Groups 14 to 16 in the periodic table.

Examples of the aromatic hydrocarbon group include residues such as benzene, naphthalene, anthracene, phenanthrene, pyrene, biphenyl, terphenyl, and fluoranthene.

Examples of the heterocyclic group include residues such as imidazole, benzoimidazole, pyrrole, furan, thiophene, benzothiophene, oxadiazoline, indoline, carbazole, pyridine, quinoline, isoquinoline, benzoquinone, pyralozine, imidazolidine, and piperidine.

Examples of the atom belonging to any one of Groups 14 to 16 in the periodic table include carbon (C), nitrogen (N), oxygen (O), silicon (Si), phosphorus (P), sulfur (S), germanium (Ge), arsenic (As), and selenium (Se) atoms. Of those, carbon, nitrogen, and oxygen atoms are preferable.

Groups each containing the atom belonging to any one of Groups 14 to 16 in the periodic table are each independently, for example, a cyano group, an alkyl group which has 1 to 12 carbon atoms and which may have a substituent, an alkylamino group which has 1 to 12 carbon atoms and which may have a substituent, an arylamino group which has 6 to 20 carbon atoms and which may have a substituent, an alkoxy group which has 1 to 12 carbon atoms and which may have a substituent, a halogenated alkoxy group which has 1 to 12 carbon atoms and which may have a substituent, an aryloxy group which has 6 to 20 carbon atoms and which may have a substituent, an aromatic hydrocarbon group which has 6 to 20 carbon atoms and which may have a substituent, a heterocyclic group which has 3 to 20 carbon atoms and which may have a substituent, a halogenated alkyl group which has 1 to 12 carbon atoms and which may have a substituent, an alkenyl group which has 2 to 12 carbon atoms and which may have a substituent, an alkynyl group which has 2 to 12 carbon atoms and which may have a substituent, or a cycloalkyl group which has 3 to 20 carbon atoms and which may have a substituent in addition to the atom itself.

Examples of the alkyl group include a methyl group, an ethyl group, a propyl group, an isopropyl group, an n-butyl group, an s-butyl group, an isobutyl group, a t-butyl group, an n-pentyl group, an n-hexyl group, an n-heptyl group, and an n-octyl group.

Examples of the aromatic hydrocarbon group include residues such as benzene, naphthalene, anthracene, phenanthrene, pyrene, biphenyl, terphenyl, and fluoranthene.

Examples of the heterocyclic group include residues such as imidazole, benzimidazole, pyrrole, furan, thiophene, benzothiophene, oxadiazoline, indoline, carbazole, pyridine, quinoline, isoquinoline, benzoquinone, pyralozine, imidazolidine, and piperidine.

Examples of the alkylamino group include groups each obtained by substituting a hydrogen atom of an amino group with the alkyl group.

Examples of the arylamino group include groups each obtained by substituting a hydrogen atom of an amino group with the aromatic hydrocarbon group.

The alkoxy group is represented as —OY''', and examples of Y' include the groups described above as the examples of the alkyl group.

Examples of the halogenated alkoxy group include groups each obtained by substituting a hydrogen atom of the alkoxy group with the halogen atom.

The aryloxy group is represented as —OY''', and examples of Y''' include the groups described above as the examples of the aromatic hydrocarbon group.

Examples of the halogenated alkyl group include groups each obtained by substituting a hydrogen atom of the alkyl group with the halogen atom.

Examples of the alkenyl group include a vinyl group, an allyl group, a 2-butenyl group, and a 3-pentenyl group.

Examples of the alkynyl group include an ethinyl group and a methylethinyl group.

Examples of the cycloalkyl group include a cyclopropyl group, a cyclobutyl group, a cyclopentyl group, and a cyclohexyl group.

$L^2$ and $L^5$ each represent, for example, a trivalent residue derived from any one of the above-mentioned specific examples, $L^6$ represents, for example, a divalent residue derived from any one of the above-mentioned specific examples, and $L^1$, $L^3$, and $L^4$ each represent, for example, a monovalent residue derived from any one of the above-mentioned specific examples.

It should be noted that an element in each of $L^1$, $L^3$, and $L^4$ directly bonded to M is an atom belonging to Group 15 in the periodic table, and the atom is preferably N or P.

An $L^1L^2L^3M$ part in the general formula (1) is preferably a structure represented by any one of the following general formulae (5) to (8).

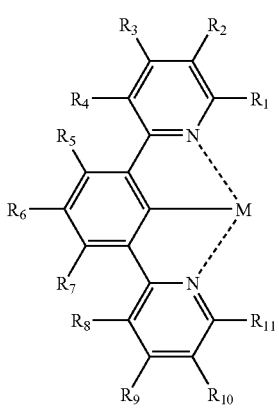

(5)

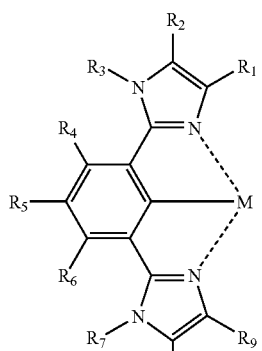

(6)

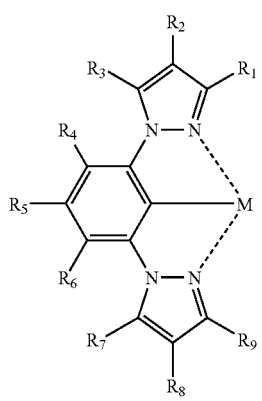

(7)

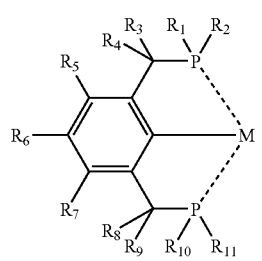

(8)

In the general formulae (5) to (8), $R_1$ to $R_{11}$ each independently represent a hydrogen atom, a cyano group, a halogen atom, an alkyl group which has 1 to 12 carbon atoms and which may have a substituent, an alkylamino group which has 1 to 12 carbon atoms, an arylamino group which has 6 to 20 carbon atoms and which may have a substituent, an alkoxy group which has 1 to 12 carbon atoms and which may have a substituent, a halogenated alkoxy group which has 1 to 12 carbon atoms and which may have a substituent, an aryloxy group which has 6 to 20 carbon atoms and which may have a substituent, an aromatic hydrocarbon group which has 6 to 20 carbon atoms and which may have a substituent, a heterocyclic group which has 3 to 20 carbon atoms and which may have a substituent, a halogenated alkyl group which has 1 to 12 carbon atoms and which may have a substituent, an alkenyl group which has 2 to 12 carbon atoms and which may have a substituent, an alkynyl group which has 2 to 12 carbon atoms and which may have a substituent, or a cycloalkyl group which has 3 to 20 carbon atoms and which may have a substituent, and adjacent groups may be bonded to each other to form a cyclic structure Examples of the halogen atom include fluorine, chlorine, bromine, and iodine atoms.

Specific examples of each of those groups except the halogen atom include the groups described above as the examples of the group containing an atom belonging to any one of Groups 14 to 16 in the periodic table represented by each of $L^1$ to $L^6$.

In addition, examples of the cyclic structure formed by the bonding of adjacent groups include: cycloalkanes (such as cyclopropane, cyclobutane, cyclopropane cyclohexane, and cycloheptane); aromatic hydrocarbon rings (such as benzene, naphthalene, anthracene, phenanthrene, pyrene, biphenyl, terphenyl, and fluoranthene); and heterocyclic rings (such as imidazole, benzimidazole, pyrrole, furan, thiophene, benzothiophene, oxadiazoline, diphenylanthracene, indoline, carbazole, pyridine, quinoline, isoquinoline, benzoquinone, pyralozine, imidazolidine, and piperidine).

An $L^4L^5L^6M$ part in the general formula (1) is preferably a structure represented by the following general formula (11) or (12).

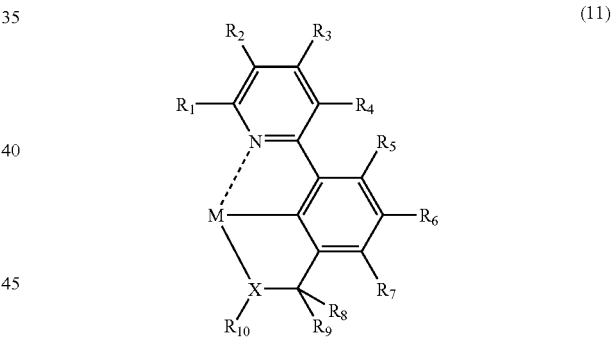

(11)

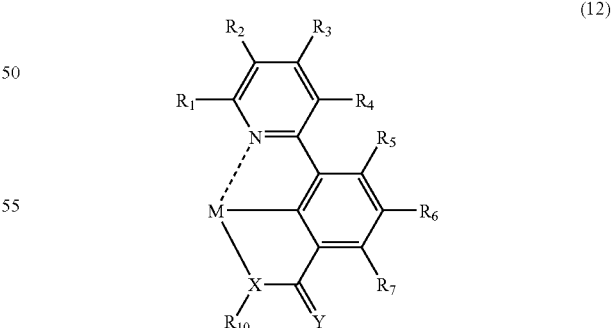

(12)

In the general formulae (11) and (12), $R_1$ to $R_{11}$ each have the same meaning as that described above, specific examples of each of $R_1$ to $R_{11}$ include examples similar to those described above, and examples of a cyclic structure formed by the bonding of adjacent groups include examples similar to those described above.

In the general formulae (11) and (12), X and Y each independently represent a group containing an atom belonging to any one of Groups 14 to 16 in the periodic table, and specific examples of each of X and Y include the groups described above as the examples of the group containing an atom belonging to any one of Groups 14 to 16 in the periodic table represented by any one of $L^1$ to $L^6$ in the general formula (1).

It should be noted that $R_{10}$ is absent when X represents an atom belonging to Group 16 in the periodic table.

Next, a metal complex compound represented by the general formula (2) having two tridentate chelate ligands will be described.

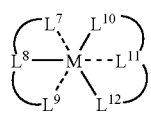

(2)

In the general formula (2), M has the same meaning as that described above, and specific examples of M include examples similar to those described above.

In the general formula (2), $L^7$ to $L^{12}$ each independently represent the same group as that represented by any one of $L^1$ to $L^6$ described above, and specific examples of the group represented by any one of $L^7$ to $L^{12}$ include the groups described above as the examples of each of $L^1$ to $L^6$, $L^8$ and $L^{10}$ to $L^{12}$ each represent, for example, a divalent residue derived from any one of the above-mentioned specific examples, and $L^7$ and $L^9$ each represent, for example, a monovalent residue derived from any one of the above-mentioned specific examples.

It should be noted that an element in each of $L^7$, $L^9$, and $L^{11}$ directly bonded to M is an atom belonging to Group 15 in the periodic table, and the atom is preferably N or P.

Further, the following structure is excluded from examples of the general formula (2).

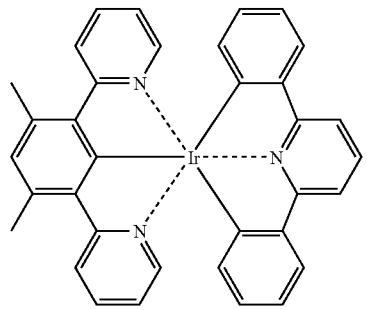

An $L^7L^8L^9$M part in the general formula (2) is preferably a structure represented by any one of the general formulae (5) to (8).

An $L^{10}L^{11}L^{12}$M part in the general formula (2) is preferably a structure represented by any one of the following general formulae (13) to (15).

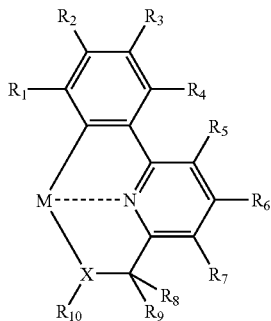

(13)

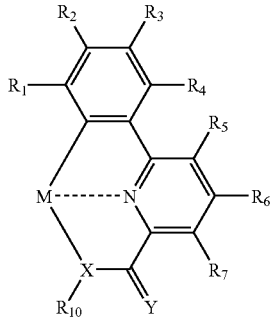

(14)

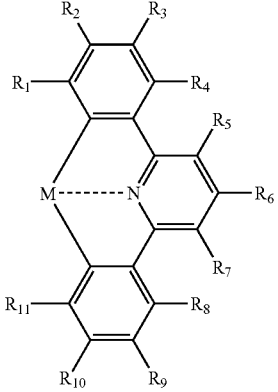

(15)

In the general formulae (13) to (15), $R_1$ to $R_{11}$, and X and Y each independently have the same meaning as that of each of the general formulae (11) and (12), specific examples of each of $R_1$ to $R_{11}$, and X and Y include examples similar to those described above, and examples of a cyclic structure formed by the bonding of adjacent groups include examples similar to those described above.

Next, a metal complex compound represented by the general formula (3) having two tridentate chelate ligands will be described.

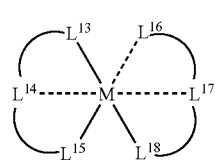

(3)

In the general formula (3), M has the same meaning as that described above, and specific examples of M include examples similar to those described above.

In the general formula (3), $L^{13}$ to $L^{18}$ each independently represent the same group as that represented by any one of $L^1$ to $L^6$ described above, specific examples of each of $L^{13}$ to $L^{18}$ include examples similar to those described above, $L^{13}$ to $L^{15}$, and $L^{17}$ and $L^{18}$ each represent, for example, a divalent residue derived from anyone of the above specific examples, and $L^{16}$ represents, for example, a monovalent residue derived from any one of the above specific examples.

It should be noted that an element in each of $L^{14}$, $L^{16}$, and $L^{17}$ directly bonded to M is an atom belonging to Group 15 in the periodic table, and the atom is preferably N or P.

An $L^{13}L^{14}L^{15}M$ part in the general formula (3) is preferably a structure represented by the following general formula (9).

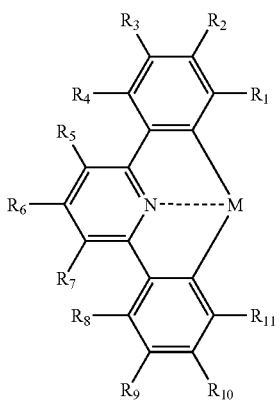

(9)

In the general formula (9) $R_1$ to $R_{11}$ each have the same meaning as that described above, specific examples of each of $R_1$ to $R_{11}$ include examples similar to those described above, and examples of a cyclic structure formed by the bonding of adjacent groups include examples similar to those described above.

An $L^{16}L^{17}L^{18}M$ part in the general formula (3) is preferably a structure represented by the following general formula (16).

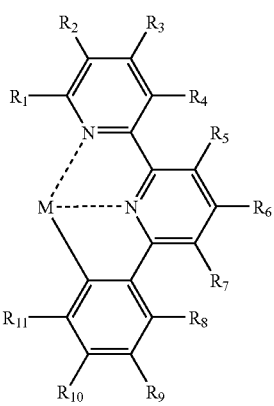

(16)

In the general formula (16), $R_1$ to $R_{11}$ each have the same meaning as that described above, specific examples of each of $R_1$ to $R_{11}$ include examples similar to those described above, and examples of a cyclic structure formed by the bonding of adjacent groups include examples similar to those described above.

Next, a metal complex compound represented by the general formula (4) having two tridentate chelate ligands will be described.

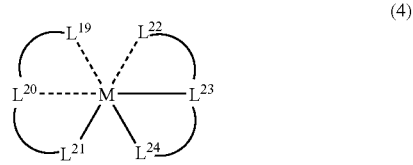

(4)

In the general formula (4), M has the same meaning as that described above, and specific examples of M include examples similar to those described above.

In the general formula (4), $L^{19}$ to $L^{24}$ each independently represent the same group as that represented by any one of $L^1$ to $L^6$ described above, specific examples of each of $L^{19}$ to $L^{24}$ include examples similar to those described above, $L^{23}$ represents, for example, a trivalent residue derived from any one of the above specific examples, $L^{20}$, $L^{21}$, and $L^{24}$ each represent, for example, a divalent residue derived from any one of the above specific examples, and $L^{19}$ and $L^{22}$ each represent, for example, a monovalent residue derived from any one of the above specific examples.

It should be noted that an element in each of $L^{19}$, $L^{20}$, and $L^{22}$ directly bonded to M is an atom belonging to Group 15 in the periodic table, and the atom is preferably N or P.

An $L^{19}L^{20}L^{21}M$ part in the general formula (4) is preferably a structure represented by the following general formula (10).

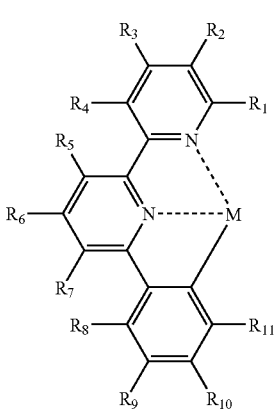

(10)

In the general formula (10), $R_1$ to $R_{11}$ each have the same meaning as that described above, specific examples of each of $R_1$ to $R_{11}$ include examples similar to those described above, and examples of a cyclic structure formed by the bonding of adjacent groups include examples similar to those described above.

An $L^{22}L^{23}L^{24}$ M part in the general formula (4) is preferably a structure represented by the following general formula (17).

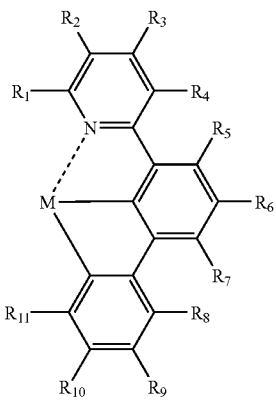

(17)

In the general formula (17), $R_1$ to $R_{11}$ each have the same meaning as that described above, specific examples of each of $R_1$ to $R_{11}$ include examples similar to those described above, and examples of a cyclic structure formed by the bonding of adjacent groups include examples similar to those described above.

It should be noted that examples of a substituent for each of the groups represented by the general formulae (1) to (17) include a halogen atom, a hydroxyl group, a substituted or unsubstituted amino group, a nitro group, a cyano group, a substituted or unsubstituted alkyl group, an alkyl group substituted with a fluorine atom, a substituted or unsubstituted alkenyl group, a substituted or unsubstituted cycloalkyl group, a substituted or unsubstituted alkoxyl group, a substituted or unsubstituted heterocyclic group, a substituted or unsubstituted arylalkyl group, a substituted or unsubstituted aryloxy group, a substituted or unsubstituted alkoxycarbonyl group, and a carboxyl group.

Specific examples of the metal complex compound of the present invention are shown below. However, the metal complex compound is not limited to these exemplified compounds.

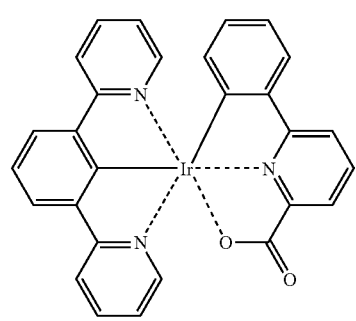

1

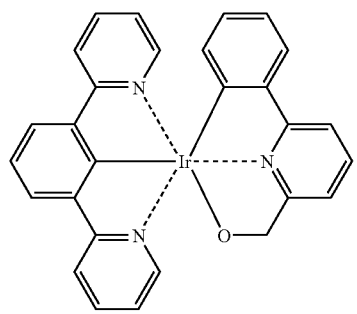

2

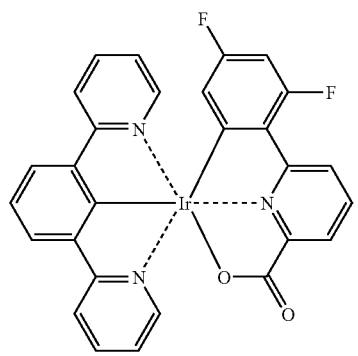

3

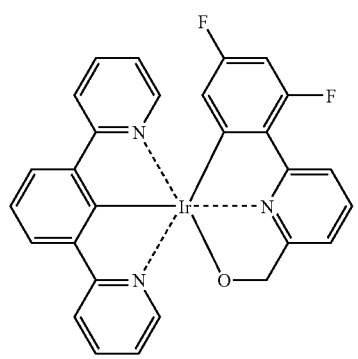

4

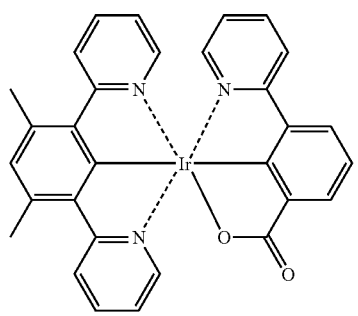

5

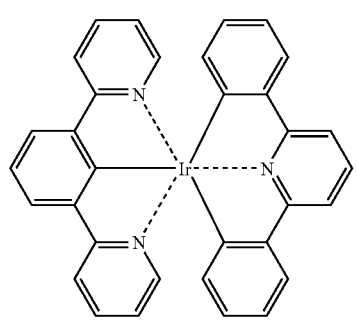

6

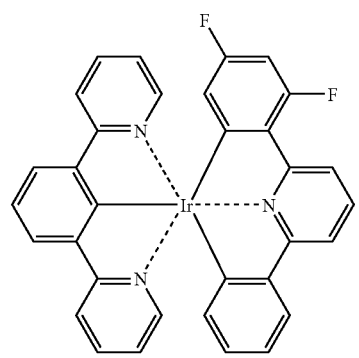
7
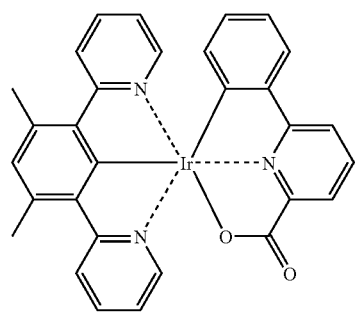
8
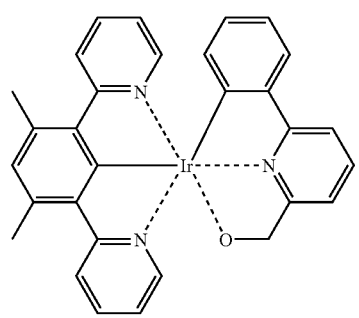
9
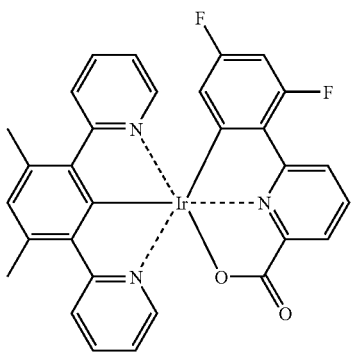
10
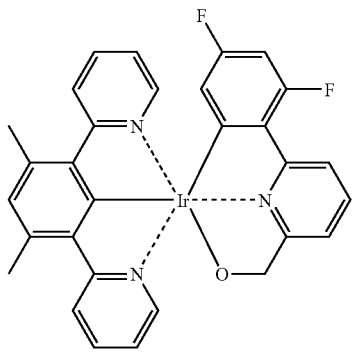
11
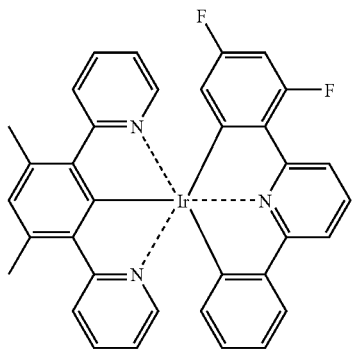
12
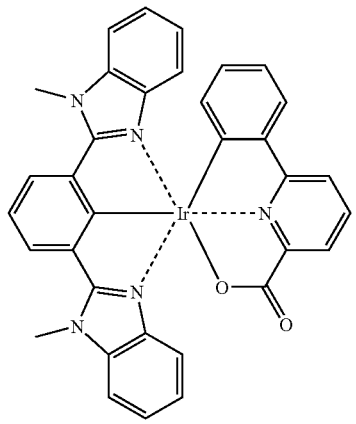
13
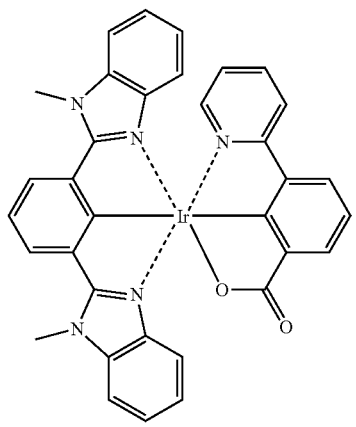
14

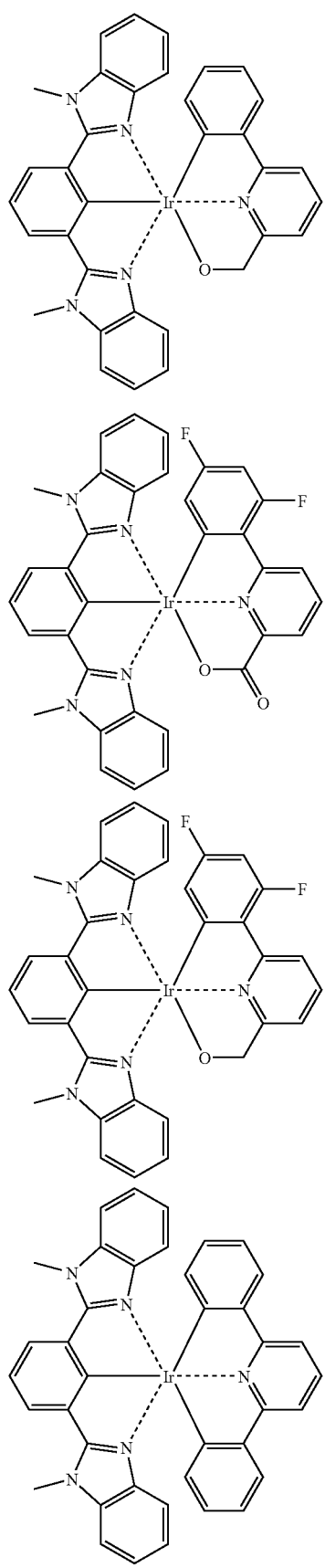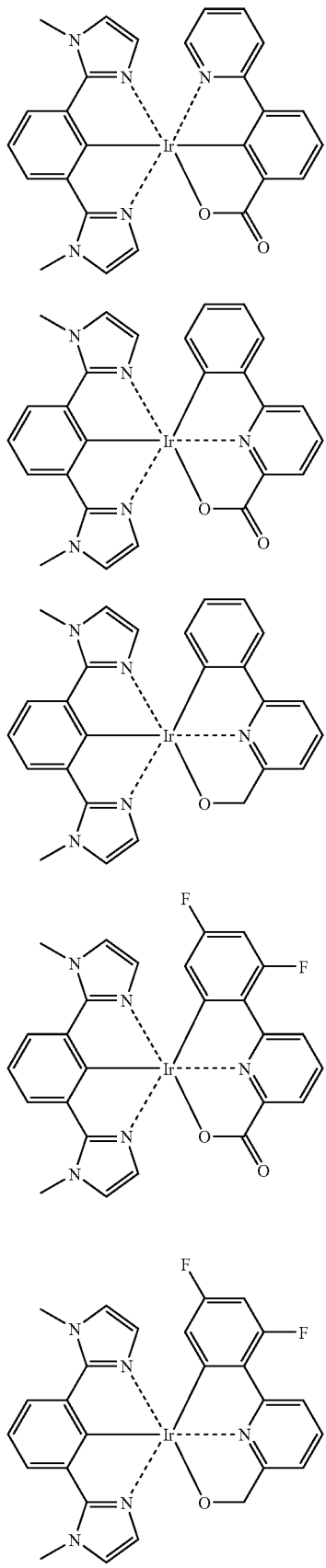

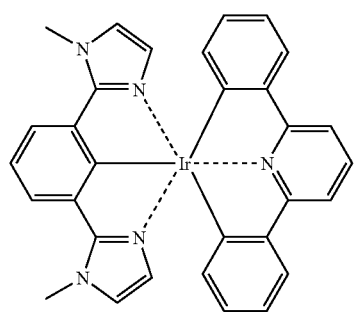
24
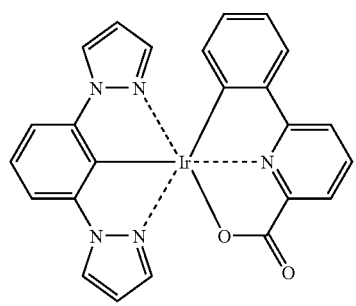
25
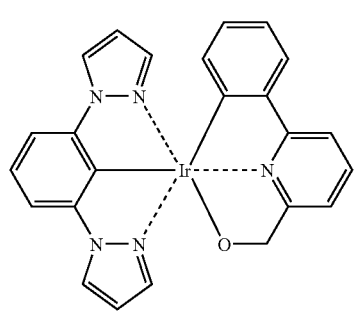
26
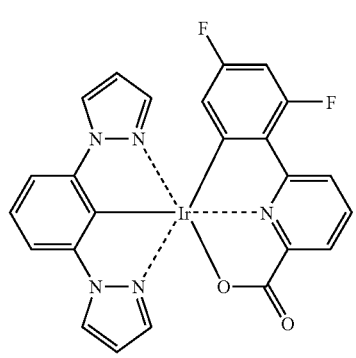
27
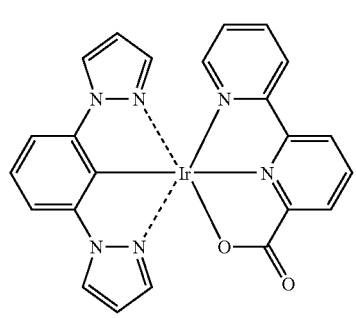
28
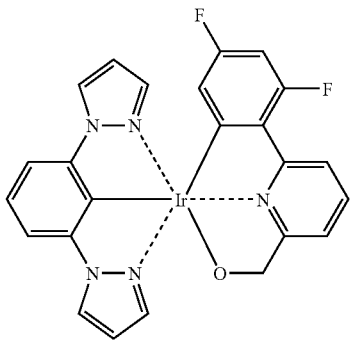
29
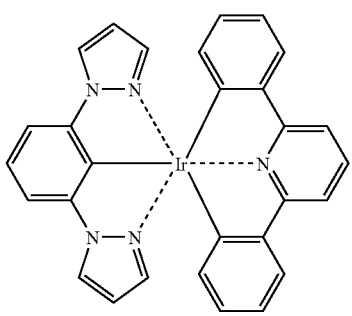
30
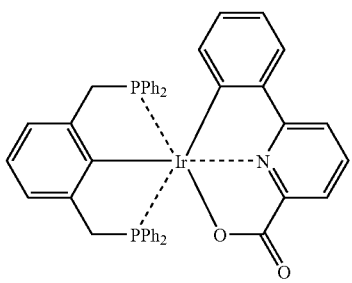
31
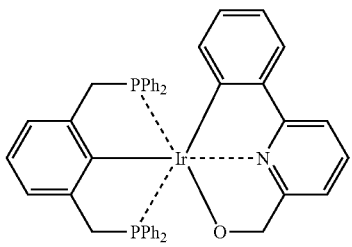
32
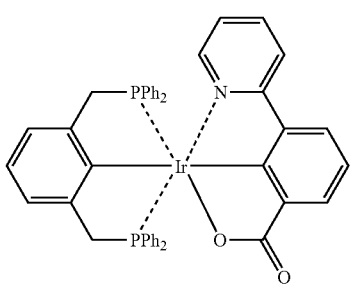
33

34
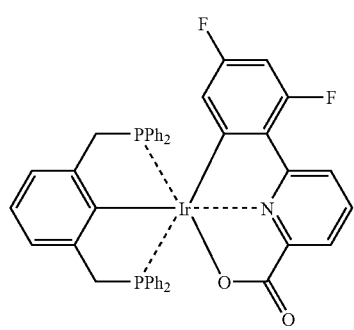
35
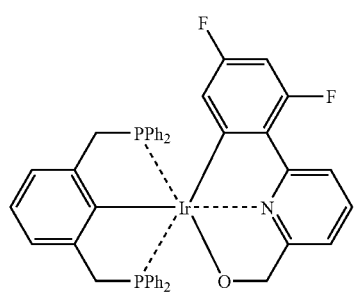
36
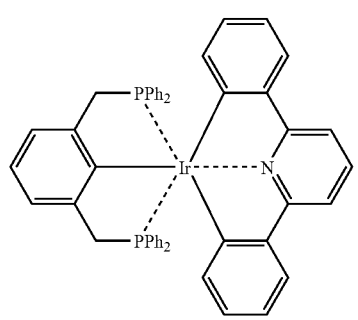
37
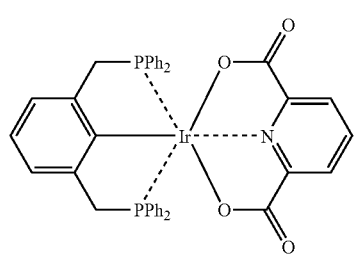
38
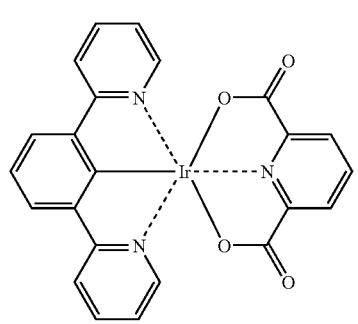
39
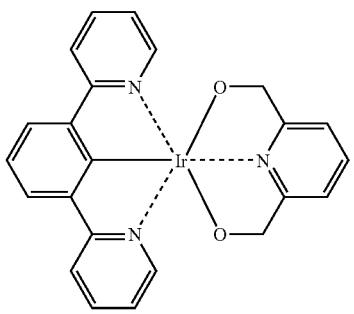
40
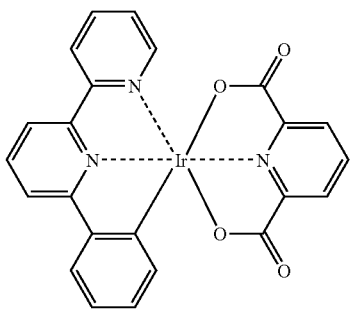
41
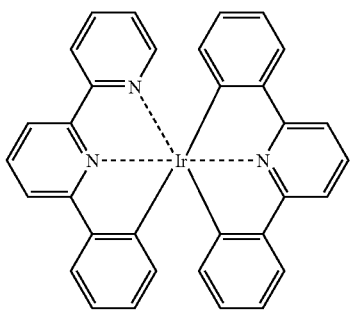
42
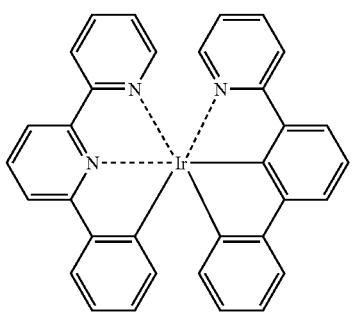
43
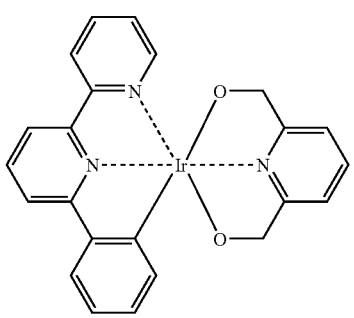
The organic EL device of the present invention includes: an organic thin film layer which has one layer or a plurality of layers including at least a light emitting layer and is disposed between a pair of electrodes consisting of a cathode and an anode, in which at least one layer of the organic thin film layer contains the metal complex compound represented by at least one kind of a compound selected from the general formulae (1) to (4) of the present invention.

The content of the metal complex compound of the present invention in the organic thin film layer is typically 0.1 to 100% by weight, or preferably 1 to 30% by weight with respect to the mass of the entirety of the light emitting layer.

In the organic EL device of the present invention, the light emitting layer preferably contains the metal complex compound of the present invention as a light emitting material or as a dopant. In addition, the light emitting layer is typically formed into a thin film by vacuum deposition or application. A layer containing the metal complex compound of the present invention is preferably formed into a film by application because the application can simplify a production process.

In the organic EL device of the present invention, when the organic thin film layer is of a single-layer type, the organic thin film layer is a light emitting layer, and the light emitting layer contains the metal complex compound of the present invention. In addition, examples of a multilayer type organic EL device include: an organic EL device having a constitution of (anode/hole injecting layer (hole transporting layer)/light emitting layer/cathode); an organic EL device having a constitution of (anode/light emitting layer/electron injecting layer (electron transporting layer)/cathode); and an organic EL device having a constitution of (anode/hole injecting layer (hole transporting layer)/light emitting layer/electron injecting layer (electron transporting layer)/cathode).

The anode of the organic EL device of the present invention supplies a hole to the hole injecting layer, the hole transporting layer, the light emitting layer, or the like, and is effective when the anode has a work function of 4.5 eV or more. Examples of a material that can be used for the anode include a metal, an alloy, a metal oxide, an electroconductive compound, and a mixture of them. Specific examples of a material for the anode include: conductive metal oxides such as tin oxide, zinc oxide, indium oxide, and indium tin oxide (ITO); metals such as gold, silver, chromium, and nickel; a mixture or laminate of the conductive metal oxides and the metals; inorganic conductive substances such as copper iodide and copper sulfide; organic conductive materials such as polyaniline, polythiophene, and polypyrrole; and a laminate of the conductive substances or materials and ITO. Of those, the conductive metal oxides are preferable, and ITO is particularly preferably used in terms of, for example, productivity, high conductivity, and transparency. The thickness of the anode can be appropriately selected depending on the material The cathode of the organic EL device of the present invention supplies an electron to the electron injecting layer, the electron transporting layer, the light emitting layer, or the like. Examples of a material that can be used for the cathode include a metal, an alloy, a metal halide, a metal oxide, an electroconductive compound, and a mixture of them. Specific examples of a material for the cathode include: alkali metals (such as Li, Na, and K), and fluorides or oxides of the metals; alkali earth metals (such as Mg and Ca), and fluorides or oxides of the metals; gold; silver; lead; aluminum; a sodium-potassium alloy or a sodium-potassium mixed metal; a lithium-aluminum alloy or a lithium-aluminum mixed metal; a magnesium-silver alloy or a magnesium-silver mixed metal; and rare earth metals such as indium and ytterbium. Of those, aluminum, the lithium-aluminum alloy or the lithium-aluminum mixed metal, the magnesium-silver alloy or the magnesium-silver mixed metal, or the like is preferable. The cathode may be structured by a single layer containing any one of the materials, or may be structured by laminating layers each containing any one of the materials. For example, the cathode is preferably of a laminate structure of aluminum/lithium fluoride or of aluminum/lithium oxide. The thickness of the cathode can be appropriately selected depending on the material.

Each of the hole injecting layer and hole transporting layer of the organic EL device of the present invention only needs to have any one of a function of injecting a hole from the anode, a function of transporting a hole, and a function of blocking an electron injected from the cathode. Specific examples of a material for each of the layers include: a carbazole derivative; a triazole derivative; an oxazole derivative; an oxadiazole derivative; an imidazole derivative; a polyarylalkane derivative; a pyrazoline derivative; a pyrazolone derivative; a phenylenediamine derivative; an arylamine derivative; an amino-substituted chalcone derivative; a styrylanthracene derivative; a fluorenone derivative; a hydrazone derivative; a stilbene derivative; a silazane derivative; an aromatic tertiary amine compound; a styrylamine compound; an aromatic dimethylidyne-based compound; a porphyrin-based compound; a polysilane-based compound; a poly(N-vinylcarbazole) derivative; an aniline-based copolymer; a conductive, high-molecular-weight oligomer such as a thiophene oligomer or polythiophene; an organic silane derivative; and the metal complex compound of the present invention. In addition, each of the hole injecting layer and the hole transporting layer may be of a single-layered structure composed of one or two or more of the materials, or may be of a multi-layered structure composed of a plurality of layers identical to or different from each other in composition.

Each of the electron injecting layer and electron transporting layer of the organic EL device of the present invention only needs to have any one of a function of injecting an electron from the cathode, a function of transporting an electron, and a function of blocking a hole injected from the anode. Specific examples of a material for each of the layers include: a triazole derivative; an oxazole derivative; an oxadiazole derivative; an imidazole derivative; a fluorenone derivative; an anthraquinodimethane derivative; an anthrone derivative; a diphenylquinone derivative; a thiopyranedioxide derivative; a carbodiimide derivative; a fluorenylidenemethane derivative; a distyrylpyrazine derivative; aromatic tetracarboxylic anhydrides such as naphthalene and perylene; various metal complexes typified by metal complexes of a phthalocyanine derivative and an 8-quinolinol derivative, a metal phthalocyanine, and a metal complex using benzoxazole or benzothiazole as a ligand; an organic silane derivative; and the metal complex compound of the present invention. In addition, each of the electron injecting layer and the electron transporting layer may be of a single-layered structure composed of one or two or more of the materials, or may be of a multi-layered structure composed of a plurality of layers identical to or different from each other in composition.

In the organic EL device of the present invention, at least one of the electron injecting layer and the electron transporting layer preferably contains a n-electron-deficient, nitrogen-containing heterocyclic derivative as a main component.

In addition, in the organic EL device of the present invention, an insulating or semi-conducting inorganic compound is preferably used as a substance constituting the electron injecting or transporting layer. When the electron injecting or transporting layer is constituted by an insulator or a semiconductor, a current leak can be effectively prevented, and electron injecting property can be improved. It is preferable that at least one metal compound selected from the group consisting of alkali metal chalcogenides, alkaline earth metal chalcogenides, alkali metal halides, and alkaline earth metal halides be used as the insulator. It is preferable that the electron injecting or transporting layer be constituted with the above-mentioned alkali metal chalcogenide or the like since the electron injecting property can be additionally improved.

To be specific, preferable examples of the alkali metal chalcogenide include $Li_2O$, $Na_2S$, and $Na_2Se$. Preferable examples of the alkaline earth metal chalcogenide include CaO, BaO, SrO, BeO, BaS, and CaSe. Preferable examples of the alkali metal halide include LiF, NaF, KF, LiCl, KCl, and NaCl. Preferable examples of the alkaline earth metal halide include fluorides such as $CaF_2$, $BaF_2$, $SrF_2$, $MgF_2$, and $BeF_2$, and halides other than the fluorides.

Further, examples of the semiconductor for constituting the electron injecting or transporting layer include oxides, nitrides, and oxide nitrides containing at least one element selected from the group consisting of Ba, Ca, Sr, Yb, Al, Ga, In, Li, Na, Cd, Mg, Si, Ta, Sb, and Zn, which are used alone or in combination of two or more. It is preferable that the inorganic compound constituting the electron transporting layer be in the form of a fine crystalline or amorphous insulating thin film. When the electron transporting layer is constituted of the above-mentioned insulating thin film, a more uniform thin film can be formed, and defective pixels such as dark spots can be decreased. Examples of the inorganic compound include the alkali metal chalcogenides, the alkaline earth metal chalcogenides, the alkali metal halides, and the alkaline earth metal halides which are described above.

In addition, in the present invention, a reducing dopant is preferably added to an interfacial region between the cathode and the organic thin film layer so that at least part of an organic layer in the interfacial region is reduced and turned into an anion. A preferable reducing dopant is at least one compound selected from the group consisting of an alkali metal, an oxide of an alkali earth metal, an alkali earth metal, a rare earth metal, an oxide of an alkali metal, a halide of an alkali metal, a halide of an alkali earth metal, an oxide or halide of a rare earth metal, an alkali metal complex, an alkali earth metal complex, and a rare earth metal complex. To be specific, a preferable reducing dopant is at least one alkali metal selected from the group consisting of Na (work function: 2.36 eV), K (work function: 2.28 eV), Rb (work function: 2.16 eV), and Cs (work function: 1.95 eV) or at least one alkali earth metal selected from the group consisting of Ca (work function: 2.9 eV), Sr (work function: 2.0 to 2.5 eV), and Ba (work function: 2.52 eV) with a reducing dopant having a work function of 2.9 eV being particularly preferable. Of those, a more preferable reducing dopant is at least one alkali metal selected from the group consisting of K, Rb, and Cs, a still more preferable reducing dopant is Rb or Cs, and the most preferable reducing dopant is Cs. Those alkali metals each have a particularly high reducing ability. The addition of a relatively small amount of each of those alkali metals to a region into which an electron is injected can improve the emission luminance and lifetime of the organic EL device.

Preferable examples of the alkali earth metal oxide include BaO, SrO, CaO, $Ba_xSr_{1-x}O$ (0<x<1) obtained by mixing BaO and SrO, and $Ba_xCa_{1-x}O$ (0<x<1) obtained by mixing BaO and CaO. Examples of an alkali oxide or an alkali fluoride include LiF, $Li_2O$, and NaF. The alkali metal complex is not particularly limited as long as it contains at least an alkali metal ion as a metal ion. The alkali earth metal complex is not particularly limited as long as it contains at least an alkali earth metal ion as a metal ion. The rare earth metal complex is not particularly limited as long as it contains at least a rare earth metal ion as a metal ion. In addition, examples of a ligand include, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzoimidazole, hydroxybenzotriazole, hydroxy fluborane, bipyridyl, phenanthroline, phthalocyanine, porphyrin, cyclopentadiene, β-diketones, azomethines, and derivatives of them.

In addition, the reducing dopant is preferably formed into a layer shape or an island shape. The thickness of the reducing dopant to be used in a layer shape is preferably 0.05 to 8 nm.

A preferable approach to forming an electron injecting or transporting layer containing the reducing dopant is a method involving: depositing organic matter as a light emitting material or electron injecting material for forming the interfacial region simultaneously with the deposition of the reducing dopant by a resistance heating deposition method; and dispersing the reducing dopant in the organic matter. A molar concentration ratio between the reducing dopant to be dispersed and the organic matter is 100:1 to 1:100, or preferably 5:1 to 1:5. Upon formation of the reducing dopant into a layer shape, the light emitting material or the electron injecting material is formed into a layer shape to serve as an interfacial organic layer, and then the reducing dopant is deposited alone by the resistance heating deposition method to be formed into a layer shape having a thickness of preferably 0.5 nm to 15 nm. Upon formation of the reducing dopant into an island shape, the light emitting material or the electron injecting material is formed to serve as an interfacial organic layer, and then the reducing dopant is deposited alone by the resistance heating deposition method to be formed into an island shape having a thickness of preferably 0.05 to 1 nm.

The light emitting layer of the organic EL device of the present invention has: a function with which a hole can be injected from the anode or the hole injecting layer and an electron can be injected from the cathode or the electron injecting layer upon application of an electric field; a function of moving injected charge (the electron and the hole) with the force of the electric field; and a function with which a field for recombination between the electron and the hole is provided so that the recombination can lead to light emission. The light emitting layer of the organic EL device of the present invention preferably contains at least the metal complex compound of the present invention, and may contain a host material using the metal complex compound as a guest material. Examples of the host material include a host material having a carbazole skeleton, a host material having a diarylamine skeleton, a host material having a pyridine skeleton, a host material having a pyrazine skeleton, a host material having a triazine skeleton, and a host material having an arylsilane skeleton. The energy level of the lowest triplet excited state (Tl) of the host material is preferably larger than the Tl level of the guest material. The host material may be a low-molecular-weight compound, or may be a high-molecular-weight compound. In addition, a light emitting layer in which the host material is doped with a light emitting material such as the metal complex compound can be formed by, for example, the co-deposition of the host material and the light emitting material.

A method of forming each of the layers in the organic EL device of the present invention is not particularly limited. Various methods such as a vacuum deposition method, an LB method, a resistance heating deposition method, an electron beam method, a sputtering method, a molecular lamination method, a coating method (such as a spin coating method, a cast method, or a dip coating method), an ink-jet method, and a printing method can be employed. In the present invention, a coating method as an application method is preferable.

Further, the organic thin film layer containing the metal complex compound of the present invention can be formed in accordance with a conventionally known method such as the vacuum deposition method, the molecular beam epitaxy method (i.e., MBE method), or the coating method such as the dipping method, the spin coating method, the casting method, a bar coat method, and a roll coat method, each of which uses a solution with a substance dissolved in a solvent.

Examples of a solvent to be used in the coating process include: halogen-based hydrocarbon-based solvents such as dichloromethane, dichloroethane, chloroform, carbon tetrachloride, tetrachloroethane, trichloroethane, chlorobenzene, dichlorobenzene, and chlorotoluene; ether-based solvents such as dibutyl ether, tetrahydrofuran, dioxane, and anisole; alcohol-based solvents such as methanol, ethanol, propanol, butanol, pentanol, hexanol, cyclohexanol, methyl cellosolve, ethyl cellosolve, and ethylene glycol; hydrocarbon-based solvents such as benzene, toluene, xylene, ethylbenzene, hexane, octane, and decane; and ester-based solvents such as ethyl acetate, butyl acetate, and amyl acetate. Of those, the halogen-based hydrocarbon-based solvents and the hydrocarbon-based solvents are preferable. In addition, one kind of those solvents may be used alone, or two or more kinds of them may be used as a mixture.

Each layer can be formed by the coating method, which involves: dissolving the metal complex compound of the present invention in a solvent to prepare an application liquid; applying the application liquid onto a desired layer (or electrode); and drying the liquid. The application liquid may contain a resin, and the resin may be in a dissolved state or in a dispersed state in the solvent. A disconjugate polymer (such as polyvinyl carbazole) or a conjugate polymer (such as a polyolefin-based polymer) can be used as the resin. To be specific, examples of the resin include polyvinyl chloride, polycarbonate, polystyrene, polymethyl methacrylate, polybutyl methacrylate, polyester, polysulfone, polyphenylene oxide, polybutadiene, poly(N-vinylcarbazole), a hydrocarbon resin, a ketone resin, a phenoxy resin, polyamide, ethyl cellulose, vinyl acetate, an ABS resin, polyurethane, a melamine resin, an unsaturated polyester resin, an alkyd resin, an epoxy resin, and a silicone resin.

In addition, the thickness of each organic layer of the organic EL device of the present invention is not particularly limited. In general, however, an excessively small thickness is apt to generate defects such as a pinhole, and an excessively large thickness requires a high applied voltage, thereby resulting in poor efficiency. Accordingly, the thickness is preferably in the range of several nanometers to 1 μm in ordinary cases.

EXAMPLES

Next, the present invention will be described in more detail by way of examples. However, the present invention is not limited to these examples.

Synthesis Example 1 (Synthesis of Metal Complex Compound 1)

A metal complex compound 1 was synthesized by the following process.

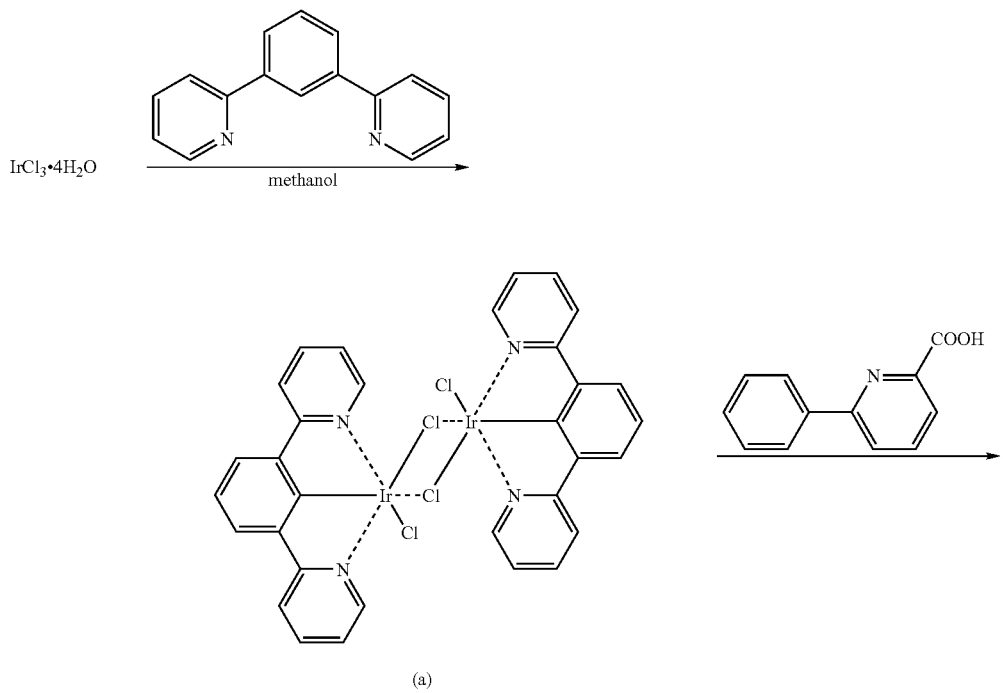

(a)

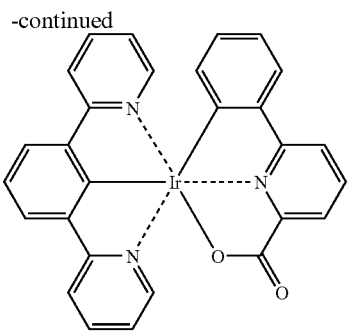

(1)

(1) Synthesis of Compound (a)

0.92 mmol (0.342 g) of iridium chloride, 0.92 mmol (0.21 g) of 1,3-(2'-pyridyl)benzene, and 20 ml of methanol were loaded into a 100-ml egg plant flask, and the whole was refluxed for 1 day in a stream of nitrogen. After having been left standing to cool, the resultant was filtered and dried, whereby 0.25 g of a yellow crystal as a target product was obtained (55% yield).

(2) Synthesis of Metal Complex Compound (1)

0.15 mmol (0.14 g) of the compound (a), 0.375 mmol (0.074 g) of 6-phenyl-2-picolinic acid, and 20 ml of glycerin were loaded into a 100-ml egg plant flask, and the whole was irradiated with a microwave from a 650-W microwave irradiation device (ZMW-007 manufactured by Shikoku Instrumentation CO., LTD.) for 10 minutes. Then, the resultant was refluxed under heat. After the resultant had been left standing to cool to room temperature, 50 ml of pure water were added to the resultant. The resultant precipitate was recovered by filtration, washed with hexane and diethyl ether, and purified with methylene chloride, whereby 0.05 g of the yellow crystal of the compound (a) was obtained (27% yield).

Synthesis Example 2 (Synthesis of Metal Complex Compound D)

The above metal complex compound D was synthesized via the following route.

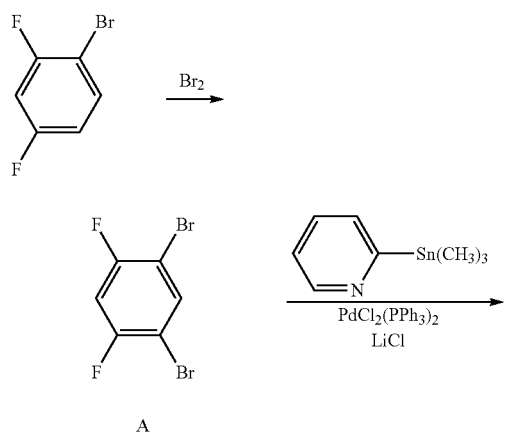

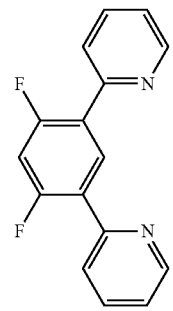

B

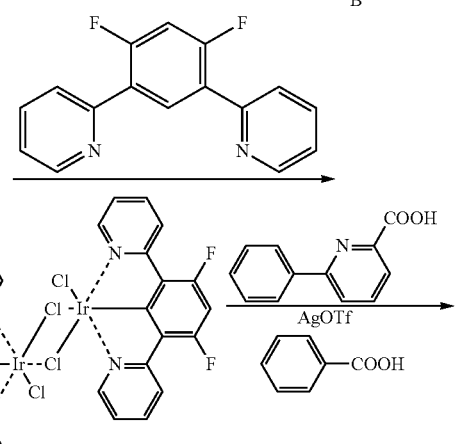

D (1) Synthesis of Compound A 39 mmol (7.52 g) of 1-bromo-2,4-difluorobenzene were loaded into a 100-ml flask, and the temperature of the 1-bromo-2,4-difluorobenzene was heated to 60° C. Next, 0.15 g of iron was added, and then 39 mmol (6.23 g) of bromine were dropped over 3 hours while the temperature of the mixture was kept at 60° C. After the completion of the dropping, the resultant was further subjected to a reaction at 60° C. for 2 hours.

After the temperature of the resultant reaction liquid had been cooled to room temperature, the reaction liquid was charged into a cold aqueous solution of sodium hydroxide, and the reaction product was extracted with hexane. An organic layer was washed with pure water and a saturated sodium chloride solution, and was dehydrated with anhydrous sodium sulfate. After that, the solvent was removed. The resultant residue was purified by means of silica gel chromatography (developing solvent: hexane), whereby 8.81 g of a compound A as colorless oil were obtained (84% yield).

(2) Synthesis of Compound B

A 200-ml three-necked flask was replaced with nitrogen. 207 mmol (8.78 g) of lithium chloride and 1.6 mmol (1.13 g) of bistriphenylphosphine palladium dichloride were added, and the flask was replaced with nitrogen again. Next, 80 ml of toluene and 20.7 mmol (5.62 g) of the compound A were added. Further, 62.1 mmol (15.0 g) of trimethyl-2-pyridyl tin were dropped, and the whole was refluxed under heat for 3 days in a stream of nitrogen. After the resultant had been left standing to cool, 150 ml of a saturated aqueous solution of potassium fluoride were added, and the whole was stirred for 30 minutes. A solid was removed by filtration, and the remainder was extracted with methylene chloride and a 5% aqueous solution of sodium hydrogen carbonate. After that, sodium sulfate was added to an organic layer for dehydration. The solvent was removed under reduced pressure, whereby a brown solid was obtained.

Ether was added to the resultant solid, and the solvent was removed by filtration, whereby 4.35 g of a compound B were obtained (78.3% yield).

(3) Synthesis of Compound C 1.3 mmol (0.469 g) of iridium chloride hydrate, 1.86 mmol (0.5 g) of the compound B, and 20 ml of 2-ethoxyethanol were added to a 100-ml two-necked flask, and the whole was stirred under heat at 110° C. for 20 hours in a stream of nitrogen. After the resultant had been left standing to cool, the solvent was removed by filtration, whereby 0.513 g of a compound C as a yellow solid was obtained (72.9% yield).

(4) Synthesis of Metal Complex Compound D 94 mmol (0.1 g) of the compound C, 94 mmol (0.189 g) of 6-phenyl-2-picolinic acid, 560 mmol (0.145 g) of silver triflate, and 7.4 mol (0.91 g) (910 mg, 7.44 mol) of benzoic acid were loaded into a mortar, and were ground.

The resultant was loaded into a 100-ml egg plant flask, and was heated at 150° C. for 24 hours in a stream of nitrogen. After having been left standing to cool, the content was dissolved in methylene chloride, the solution was washed with a 1M sodium carbonate solution, and an organic layer was subjected to Celite filtration. Next, the solvent was removed under reduced pressure, and the remainder was washed with ether, whereby 35 mg of a compound D as a yellow solid were obtained (57% yield).

$^1$H-NMR (500 MHz, DMSO-d6): δ 8.52 (1H, d, J=8.0), 8.27 (1H, t, J=8.0), 8.14 (2H, d, J=8.6), 8.03 (1H, t, J=6.0), 7.91 (2H, t, J=7.7), 7.83 (1H, d, J=7.4), 7.38 (2H, t, J=4.6), 7.24 (1H, t, J=11.7), 7.13 (2H, t, J=6.3), 6.74 (1H, q, J=5.5), 6.55 (1H, t, J=8.0), 5.57 (1H, d, 8.0).

Investigation into the light emitting property of this compound resulted in a spectrum having a peak at 485 nm at room temperature (methylene chloride solution) (see FIG. 1).

UV absorption spectrum (λmax/nm(ε/mol$^{-1}$ dm$^3$ cm$^{-1}$)): 240 (49.8), 267 (43.1), 284 sh, 313 sh, 359 sh, 386 (10.1), 409 (10.5), 439 sh, 472 (2.2).

Example 1 (Production of Organic EL Device)

A glass substrate equipped with a transparent electrode after being washed was mounted on the substrate holder of a vacuum deposition device. First, a copper phthalocyanine film (CuPc film) having a thickness of 10 nm was formed on the surface on the side where the transparent electrode was formed in such a manner that the film would cover the transparent electrode. The CuPc film functions as a hole injecting layer. Subsequently, NPD shown below was formed into a film having a thickness of 30 nm on the CuPc film. The NPD film functions as a hole transporting layer. Further, the following host material (CBP) was deposited from the vapor in such a manner that a light emitting layer having a thickness of 30 nm would be formed on the NPD film. The metal complex compound (1) was added as a phosphorescent Ir metal complex dopant simultaneously with the formation. The concentration of the compound (1) in the light emitting layer was set to 6% by weight. BAlq shown below was formed into a film having a thickness of 10 nm on the light emitting layer. The BAlq film functions as a hole blocking layer. Further, Alq shown below was formed into a film having a thickness of 30 nm on the BAlq film. The Alq film functions as an electron injecting layer. After that, LiF as an alkali metal halide was deposited from the vapor to have a thickness of 0.15 nm, and then aluminum was deposited from the vapor to have a thickness of 150 nm. The Al/LiF film functions as a cathode. Thus, an organic EL device was produced The device was subjected to a current test at a voltage of 6.5 V. As a result, the device was observed to emit green light.

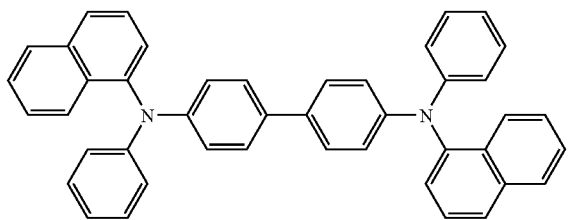

NPD

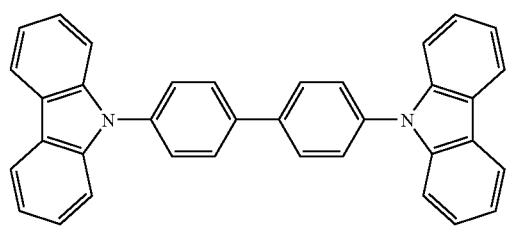

CBP

-continued

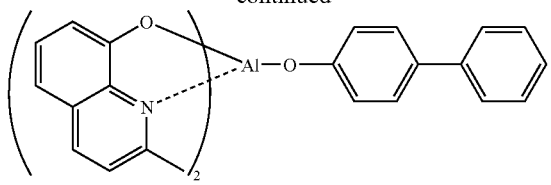
BAlq

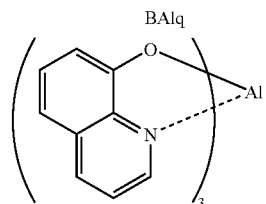
Alq

INDUSTRIAL APPLICABILITY

As described above in detail, the use of the metal complex compound of the present invention as a material for an organic EL device can provide an organic EL device whose wavelength of light emission is shortened so that blue light emission is obtained, which exhibits high efficiency of light emission, and which has a long lifetime. Accordingly, the device is applicable to fields such as various display devices, displays, back lights, light sources for illumination, marking signs, signboards, and interior lighting, and is particularly suitable as a display device for color display.

The invention claimed is:

1. A metal complex compound, which is represented by formula (1), comprising two tridentate chelate ligands

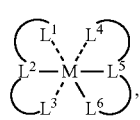
(1)

wherein:
a solid line represents a covalent bond, and a dotted line represents a coordinate bond;
M represents a trivalent metal atom selected from the group consisting of Co, Rh and Ir;
an $L^1L^2L^3M$ part comprises a structure represented by formula (5)

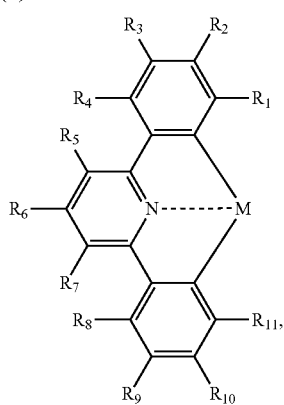
(5)

wherein:
M is as defined above; and
$R_1$ to $R_{11}$ each independently represent a hydrogen atom, a cyano group, a halogen atom, an alkyl group which has 1 to 12 carbon atoms and which may have a substituent, an alkylamino group which has 1 to 12 carbon atoms, an arylamino group which has 6 to 20 carbon atoms and which may have a substituent, an alkoxy group which has 1 to 12 carbon atoms and which may have a substituent, a halogenated alkoxy group which has 1 to 12 carbon atoms and which may have a substituent, an aryloxy group which has 6 to 20 carbon atoms and which may have a substituent, an aromatic hydrocarbon group which has 6 to 20 carbon atoms and which may have a substituent, a heterocyclic group which has 3 to 20 carbon atoms and which may have a substituent, a halogenated alkyl group which has 1 to 12 carbon atoms and which may have a substituent, an alkyl group which has 2 to 12 carbon atoms and which may have a substituent, an alkyl group which has 2 to 12 carbon atoms and which may have a substituent, or a cycloalkyl group which has 3 to 20 carbon atoms and which may have a substituent, and adjacent groups may be bonded to each other to form a cyclic structure; and
an $L^4L^5L^6M$ part comprises a structure represented by formula (12)

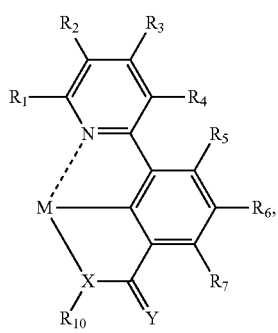
(12)

wherein:
M is as defined above;
$R_1$ to $R_7$ each independently represent a hydrogen atom, a cyano group, a halogen atom, an alkyl group which has 1 to 12 carbon atoms and which may have a substituent, an alkylamino group which has 1 to 12 carbon atoms, an arylamino group which has 6 to 20 carbon atoms and which may have a substituent, an alkoxy group which has 1 to 12 carbon atoms and which may have a substituent, a halogenated alkoxy group which has 1 to 12 carbon atoms and which may have a substituent, an aryloxy group which has 6 to 20 carbon atoms and which may have a substituent, an aromatic hydrocarbon group which has 6 to 20 carbon atoms and which may have a substituent, a heterocyclic group which has 3 to 20 carbon atoms and which may have a substituent, a halogenated alkyl group which has 1 to 12 carbon atoms and which may have a substituent, an alkenyl group which has 2 to 12 carbon atoms and which may have a substituent, an alkynyl group which has 2 to 12 carbon atoms and which may have a substituent, or a cycloalkyl group which has 3 to 20 carbon atoms and which may have a substituent, and adjacent groups may be bonded to each other to form a cyclic structure;

X represents O;

Y represents a group comprising an atom selected from the group consisting of C, N, O, Si, P, S, Ge, As, and Se; and $R_{10}$ is absent.

2. A metal complex compound, which is represented by formula (2), comprising two tridentate chelate ligands

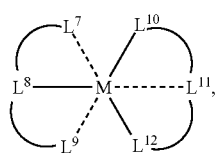

(2)

wherein:

a solid line represents a covalent bond, and a dotted line represents a coordinate bond;

M represents a trivalent metal atom selected from the group consisting of Co, Rh and Ir;

an $L^7L^8L^9M$ part comprises a structure represented by formula (5)

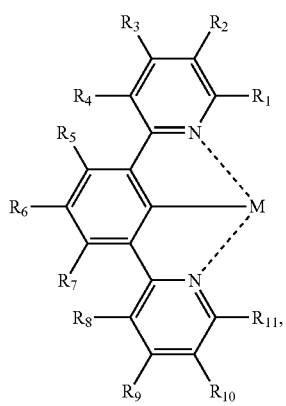

(5)

wherein:

M is as defined above; and $R_1$ to $R_{11}$ each independently represent a hydrogen atom, a cyano group, a halogen atom, an alkyl group which has 1 to 12 carbon atoms and which may have a substituent, an alkylamino group which has 1 to 12 carbon atoms, an arylamino group which has 6 to 20 carbon atoms and which may have a substituent, an alkoxy group which has 1 to 12 carbon atoms and which may have a substituent, a halogenated alkoxy group which has 1 to 12 carbon atoms and which may have a substituent, an aryloxy group which has 6 to 20 carbon atoms and which may have a substituent, an aromatic hydrocarbon group which has 6 to 20 carbon atoms and which may have a substituent, a heterocyclic group which has 3 to 20 carbon atoms and which may have a substituent, a halogenated alkyl group which has 1 to 12 carbon atoms and which may have a substituent, an alkenyl group which has 2 to 12 carbon atoms and which may have a substituent, an alkynyl group which has 2 to 12 carbon atoms and which may have a substituent, or a cycloalkyl group which has 3 to 20 carbon atoms and which may have a substituent, and adjacent groups may be bonded to each other to form a cyclic structure;

an $L^{10}L^{11}L^{12}M$ part comprises a structure represented by formula (13) or (14):

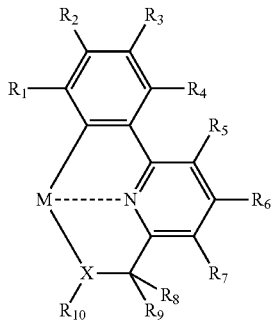

(13)

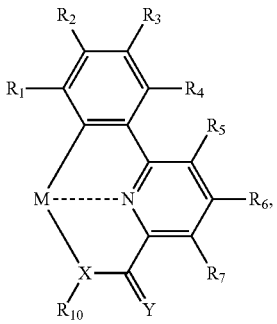

(14)

wherein:

M is as defined above; and $R_1$ to $R_9$ each independently represent a hydrogen atom, a cyano group, a halogen atom, an alkyl group which has 1 to 12 carbon atoms and which may have a substituent, an alkylamino group which has 1 to 12 carbon atoms, an arylamino group which has 6 to 20 carbon atoms and which may have a substituent, an alkoxy group which has 1 to 12 carbon atoms and which may have a substituent, a halogenated alkoxy group which has 1 to 12 carbon atoms and which may have a substituent, an aryloxy group which has 6 to 20 carbon atoms and which may have a substituent, an aromatic hydrocarbon group which has 6 to 20 carbon atoms and which may have a substituent, a heterocyclic group which has 3 to 20 carbon atoms and which may have a substituent, a halogenated alkyl group which has 1 to 12 carbon atoms and which may have a substituent, an alkenyl group which has 2 to 12 carbon atoms and which may have a substituent, an alkynyl group which has 2 to 12 carbon atoms and which may have a substituent, or a cycloalkyl group which has 3 to 20 carbon atoms and which may have a substituent, and adjacent groups may be bonded to each other to form a cyclic structure;

X represents O;

Y represents a group comprising an atom selected from the group consisting of C, N, O, Si, P, S, Ge, As, and Se;

R₁₀ is absent; and
a structure excluded from examples of formula (2) is

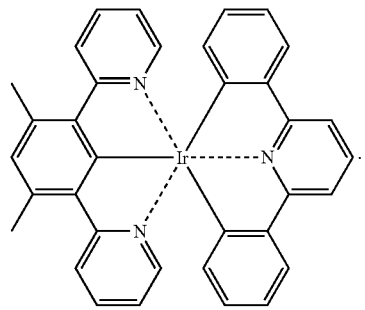

3. An organic electroluminescence device, comprising an organic thin film layer which has one layer or a plurality of layers including at least a light emitting layer and is disposed between a pair of electrodes, wherein:
at least one layer of the organic thin film layer comprises the metal complex compound according to claim 1; and
light is emitted by applying a voltage between both the electrodes.

4. An organic electroluminescence device according to claim 3, wherein the light emitting layer comprises the metal complex compound.

5. An organic electroluminescence device according to claim 3, wherein the organic electroluminescence device emits blue light.

6. An organic electroluminescence device according to claim 3, wherein the layer comprises the metal complex compound is formed by application.

7. A metal complex compound according to claim 2, wherein the $L^{10}L^{11}L^{12}M$ part comprises a structure represented by formula (13).

8. An organic electroluminescence device, comprising an organic thin film layer which has one layer or a plurality of layers including at least a light emitting layer and is disposed between a pair of electrodes, wherein:
at least one layer of the organic thin film layer comprises the metal complex compound according to claim 2; and
light is emitted by applying a voltage between both the electrodes.

9. An organic electroluminescence device according to claim 8, wherein the light emitting layer comprises the metal complex compound.

10. An organic electroluminescence device according to claim 8, wherein the organic electroluminescence device emits blue light.

11. An organic electroluminescence device according to claim 8, wherein the layer comprises the metal complex compound is formed by application.

12. The metal complex compound according to claim 1, wherein Y represents O.

13. The metal complex compound according to claim 1, wherein M is Ir.

14. The metal complex compound according to claim 1, wherein M is Co.

15. The metal complex compound according to claim 1, wherein M is Rh.

16. A metal complex compound according to claim 2, wherein the $L^{10}L^{11}L^{12}M$ part comprises a structure represented by formula (14).

17. The metal complex compound according to claim 2, wherein Y represents O.

18. The metal complex compound according to claim 2, wherein $R^8$ and $R^9$ represent H.

19. The metal complex compound according to claim 2, wherein M is Ir.

20. The metal complex compound according to claim 2, wherein M is Co.

21. The metal complex compound according to claim 2, wherein M is Rh.

22. A metal complex compound, selected from the following formulae (1)-(4), (5) and (8)-(11):

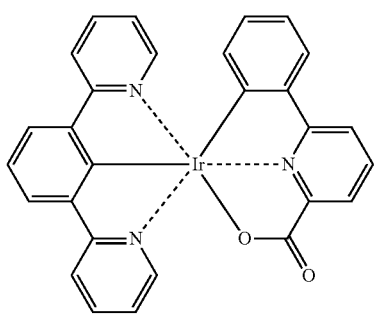

1

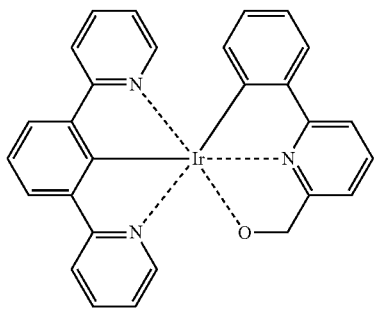

2

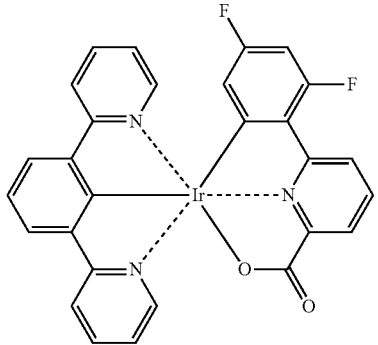

3

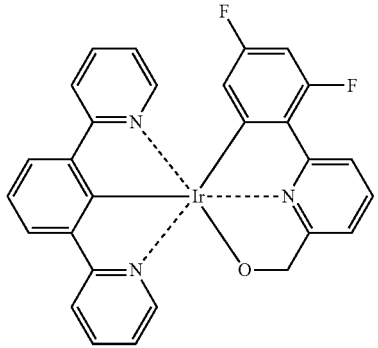

4

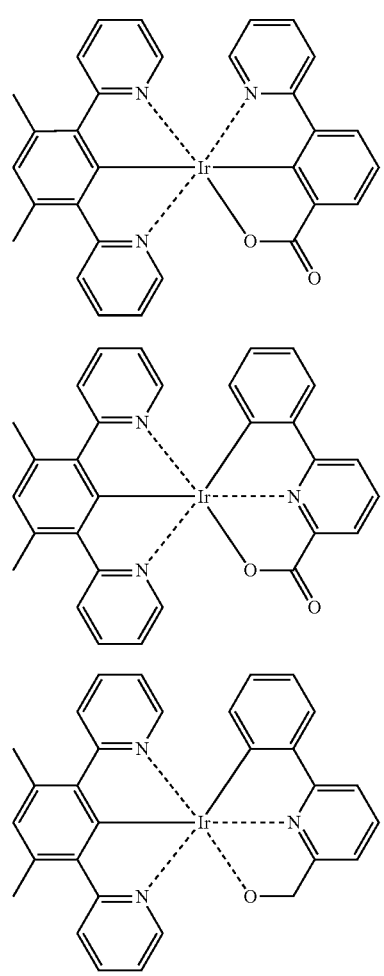
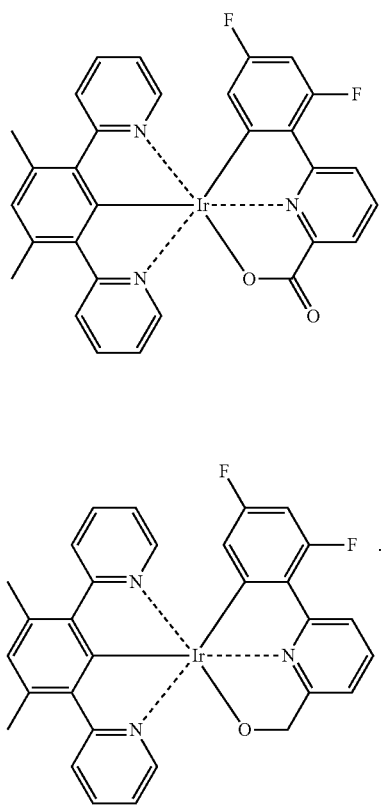
* * * * *